(12) United States Patent
Patel et al.

(10) Patent No.: US 11,832,858 B2
(45) Date of Patent: *Dec. 5, 2023

(54) SYSTEM AND METHOD FOR FASTENING OF TWO OR MORE INTERACTING ELEMENTS

(71) Applicant: The Regents of the University of Colorado, Denver, CO (US)

(72) Inventors: Vikas Patel, Denver, CO (US); Jay Nanninga, Monrovia, MD (US)

(73) Assignee: The Regents of the University of Colorado, Denver, CO (US)

(*) Notice: Subject to any disclaimer, the term of this patent is extended or adjusted under 35 U.S.C. 154(b) by 387 days.

This patent is subject to a terminal disclaimer.

(21) Appl. No.: 17/002,372

(22) Filed: Aug. 25, 2020

(65) Prior Publication Data

US 2020/0383709 A1 Dec. 10, 2020

Related U.S. Application Data

(63) Continuation of application No. 15/325,822, filed as application No. PCT/US2015/040729 on Jul. 16, 2015, now Pat. No. 10,786,289.

(60) Provisional application No. 62/025,163, filed on Jul. 16, 2014.

(51) Int. Cl.
*A61B 17/80* (2006.01)

(52) U.S. Cl.
CPC .............................. *A61B 17/8057* (2013.01)

(58) Field of Classification Search
CPC ............ A61B 17/8057; A61B 17/8052; A61B 17/8033; A61B 17/8019; A61F 2/44–4495

USPC .................................................. 606/289–295
See application file for complete search history.

(56) References Cited

U.S. PATENT DOCUMENTS

| | | | | |
|---|---|---|---|---|
| 5,951,557 A * | 9/1999 | Luter | ..................... | A61B 17/80 606/71 |
| 7,214,227 B2 * | 5/2007 | Colleran | ............ | A61B 17/7037 606/273 |
| 8,211,145 B2 * | 7/2012 | Dalton | ................ | A61B 17/8023 606/280 |
| 8,273,109 B2 * | 9/2012 | Jackson | ................ | F16B 35/047 606/273 |
| 8,585,743 B2 * | 11/2013 | Ampuero | ........... | A61B 17/8695 606/301 |

(Continued)

*Primary Examiner* — Matthew J Lawson
(74) *Attorney, Agent, or Firm* — Nicholas Pfeifer; Smith & Hopen, P. A.

(57) ABSTRACT

A method for securing a first interacting element to a second interacting element is provided. The first interacting element includes a lateral surface established by a first surface and a second surface and at least a portion of the lateral surface includes a thread receipt. The second interacting element includes a distal end and a proximal end that establishes a body therebetween. The body has a thread that is configured to at least partially engage with the thread receipt of the first interacting element. The second interacting element is then inserted at least partially through the surface of an object. The thread receipt of the first interacting element is then abutted adjacent to the thread of the second interacting element. Upon rotation of the second interacting element the thread of the second interacting element at least partially engaged with the thread receipt of the first interacting element.

11 Claims, 18 Drawing Sheets

(56) References Cited

U.S. PATENT DOCUMENTS

| | | | | |
|---|---|---|---|---|
| 9,510,867 | B2* | 12/2016 | Garamszegi | A61B 17/7059 |
| 2003/0187441 | A1* | 10/2003 | Bolger | A61B 17/8019 |
| | | | | 606/295 |
| 2006/0129149 | A1* | 6/2006 | Iott | A61B 17/7032 |
| | | | | 606/272 |
| 2007/0055235 | A1* | 3/2007 | Janowski | A61B 17/7032 |
| | | | | 606/272 |
| 2007/0073297 | A1* | 3/2007 | Reynolds | A61B 17/8052 |
| | | | | 606/280 |
| 2008/0015592 | A1* | 1/2008 | Long | A61B 17/8014 |
| | | | | 606/279 |
| 2010/0262193 | A1* | 10/2010 | Frigg | A61B 17/8019 |
| | | | | 606/281 |
| 2011/0009966 | A1* | 1/2011 | Michelson | A61F 2/4455 |
| | | | | 623/17.11 |
| 2012/0150239 | A1* | 6/2012 | Garamszegi | A61B 17/8052 |
| | | | | 606/328 |
| 2012/0253409 | A1* | 10/2012 | Peterson | A61B 17/7037 |
| | | | | 606/305 |
| 2014/0052255 | A1* | 2/2014 | DeFalco | A61B 17/8057 |
| | | | | 606/286 |
| 2017/0265914 | A1* | 9/2017 | Wiederkehr | A61B 17/8047 |

* cited by examiner

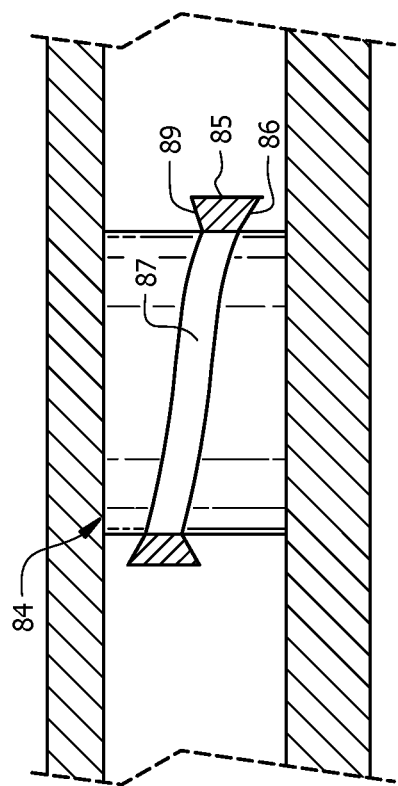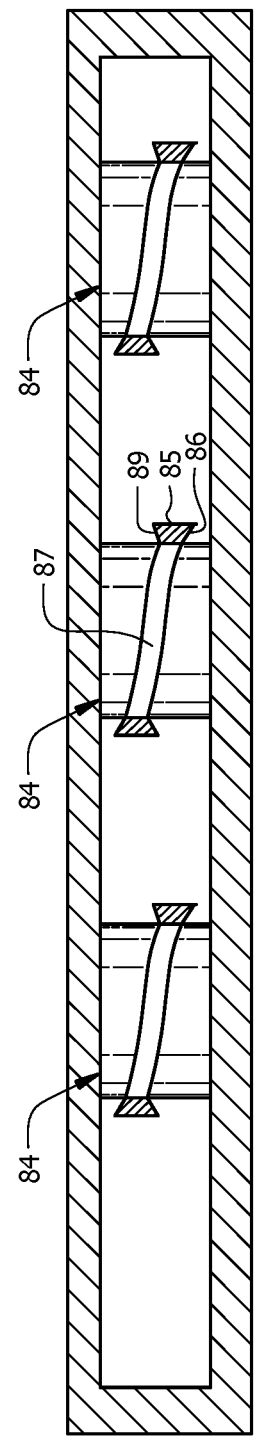
FIG. 6A
FIG. 6B

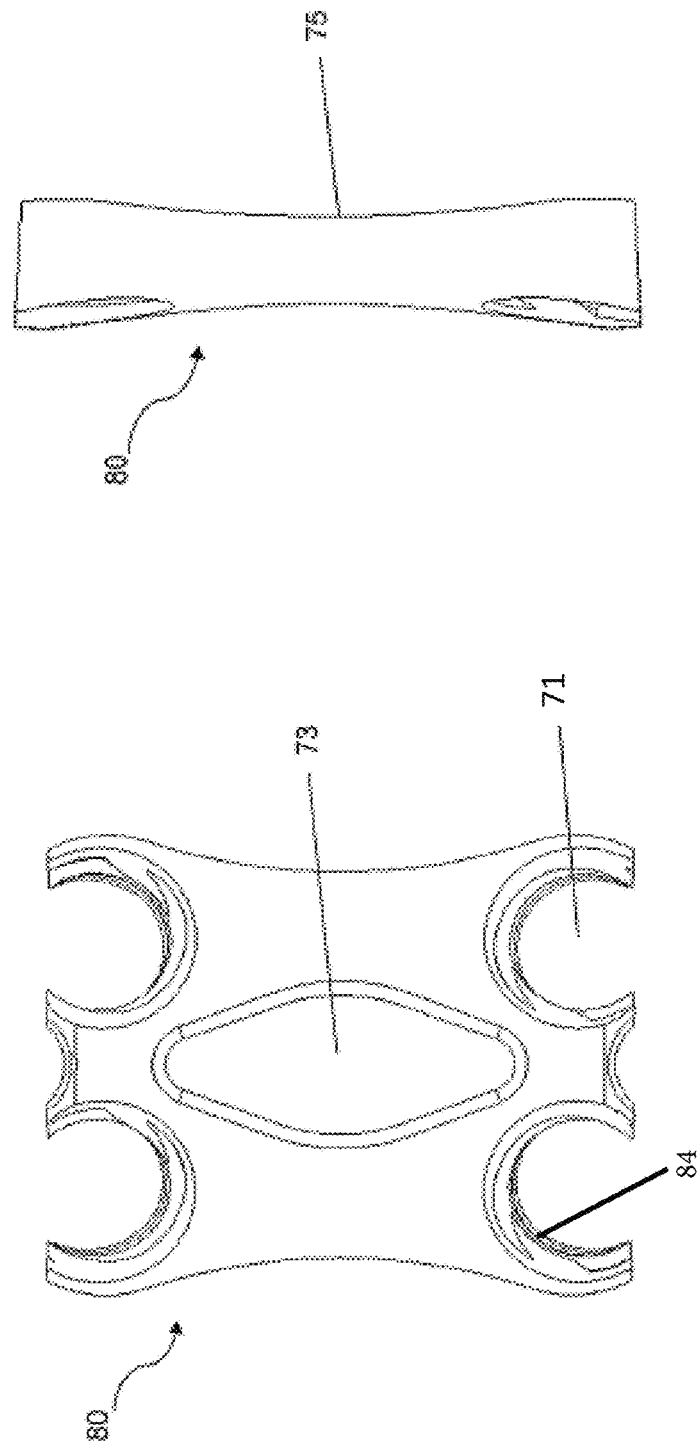
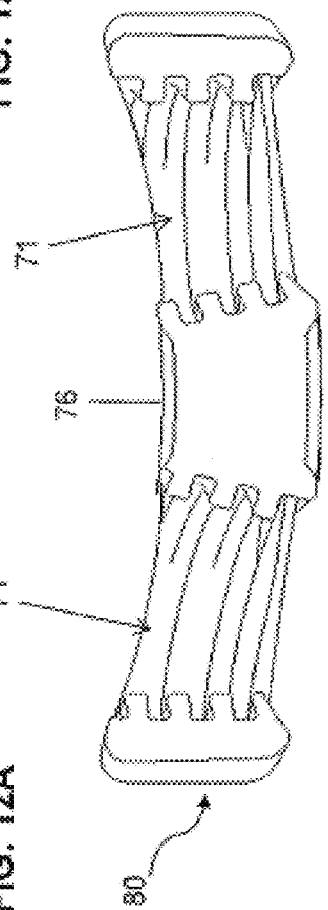
FIG. 12A  FIG. 12B  FIG. 12C

SYSTEM AND METHOD FOR FASTENING OF TWO OR MORE INTERACTING ELEMENTS

CROSS-REFERENCE TO RELATED APPLICATIONS

This nonprovisional application is a continuation of and claims priority to Non-provisional application Ser. No. 15/325,822, entitled "SYSTEM AND METHODS FOR POSITIONING OF TWO OR MORE INTERACTING ELEMENTS," filed Jan. 12, 2017, which claims priority to the PCT Application No. PCT/US15/40729, entitled "SYSTEM AND METHODS FOR POSITIONING OF TWO OR MORE INTERACTING ELEMENTS", filed Jul. 16, 2015, which claims priority to U.S. Provisional Patent Application 62/025,163, entitled "SYSTEM AND METHODS FOR POSITIONING OF TWO OR MORE INTERACTING ELEMENTS," filed Jul. 16, 2014.

BACKGROUND OF THE INVENTION

1. Field of the Invention

The present invention relates generally to system and methods for positioning two or more interacting elements.

2. Brief Description of the Prior Art

From time to time, a consumer may be motivated to position two or more interacting elements such that they are configured to maintain a particular position for a considerable period of time, such as a few minutes, a few hours, a few days, or a few weeks. As an example, if a human or animal breaks or fractures a bone, the treatment may include positioning one or more interacting elements relative to the bone to stabilize the bone in an optimized position for healing.

One or more interacting elements may include, for example, a plate and one or more fastener elements for attachment to vertebrae in order to immobilize, stabilize and/or align those vertebrae. The plate may be used for a variety of conditions including, for example, providing added strength and rigidity after fusion of adjacent vertebrae, securing vertebrae together where an intervening vertebrae has been removed and replaced, correcting spinal deformities, and correcting instability caused by trauma, fractures, tumors, advanced degenerative discs, infection, or congenital or acquired deformities.

Plates used for these types of conditions generally span the distance between two, three, four, or more vertebrae, as required in a given situation. The plate generally curves so as to fit the curvature of the vertebrae to which they are attached. Additionally, a plate of this type generally matches the curvature of the cervical spine. A plate of this type is typically provided with holes for fastener elements known as "bone screws." Pilot holes are drilled into the adjacent vertebrae by instruments that are known in the art, such as surgical drills, after which the plate is attached by the bone screws which pass through the pilot holes in the plate for securing the plate to the adjacent vertebrae.

While certain systems for stabilizing a bone exist, such known systems are associated with certain disadvantages. Thus, there is a demand for improved systems and methods for positioning two or more interacting elements relative to one another such as a plate and one or more fastener elements, for use in applications such as stabilizing fractures and cervical fixation to name a few. The present invention satisfies this demand.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

For purposes of this application, the present invention is discussed in reference to one or more interacting elements configured to stabilize the position of an object in the form of a plate and one or more fastener elements, but the discussion is merely exemplary. The present invention is applicable to any system in which two or more interacting elements are configured to maintain a particular configuration and/or position.

Certain embodiments of the system and method of the present invention include a fastener element with a body component and a thread component. Other embodiments of a fastener element may include multiple body components, each of which may include a respective thread component. Certain embodiments of a thread component may be configured to maximize the amount of weight the connection between the two interacting components can bear. Other embodiments may be configured to maximize the flexibility of the connection between the two interacting components. In some embodiments, the thread component is helical. In some embodiments, the thread component is semicircular.

One object of certain embodiments of the present invention is that it permits inserting a second interacting element, such as a fastener element, into a first interacting element, such as a plate, so that the first surface of the second interacting element is flush with or remains below the first surface of a first interacting element.

Another object of certain embodiments of the present invention is that it facilitates a removable connection between a first interacting element and a second interacting element, wherein the second interacting element is connected along the lateral surface of the first interacting element; for example, a fastener element connected along the lateral edge of the plate.

Advantageously, in embodiments in which the first interacting element is a plate for setting bones, such embodiments permit positioning the plate close to a joint without impinging the adjacent bone in the joint. Another advantage of such embodiments is that it may use smaller plates for setting bones relative to other connection methods while maintaining the strength of the connection. Alternatively, the connection may be a stronger and more rigid interface between the first interacting element and the second interacting element relative to other connection methods.

Another object of certain embodiments of the present invention is to include a first thread component that wraps around a first body component (in a generally helical shape at the same (or different) pitch as a second thread component wrapped around a second body component. For purposes of this application, the pitch of a helix is the width of one complete helix turn, measured parallel to the axis of the helix.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to the limit the invention, where like designations denote like elements, and in which:

FIG. 6A illustrates a side view of an embodiment of a first interacting element in the form of a plate, including a thread receiving element.

FIG. 6B illustrates a side view of an embodiment of a first interacting element in the form of a plate, including a plurality of thread receiving elements.

FIG. 12A illustrates a top view of a first interacting element in the form of a plate.

FIG. 12B illustrates a side view of a first interacting element.

FIG. 12C illustrates a cross-section view of an embodiment of a first interacting element.

DETAILED DESCRIPTION OF THE INVENTION

For convenience of description, terms such as "above", "below", "upper", "lower", "outer", "inner", "bottom" and "top" are used in this application to refer to the system and the components of the system in an orientation illustrated in the accompanying drawings. However, it will be understood that the embodiments of the invention described in this application advantageously can be used in a variety of orientations.

Certain embodiments of the system 10 and method of the present invention include a first interacting element 40A and a second interacting element 40B.

Figure 1:
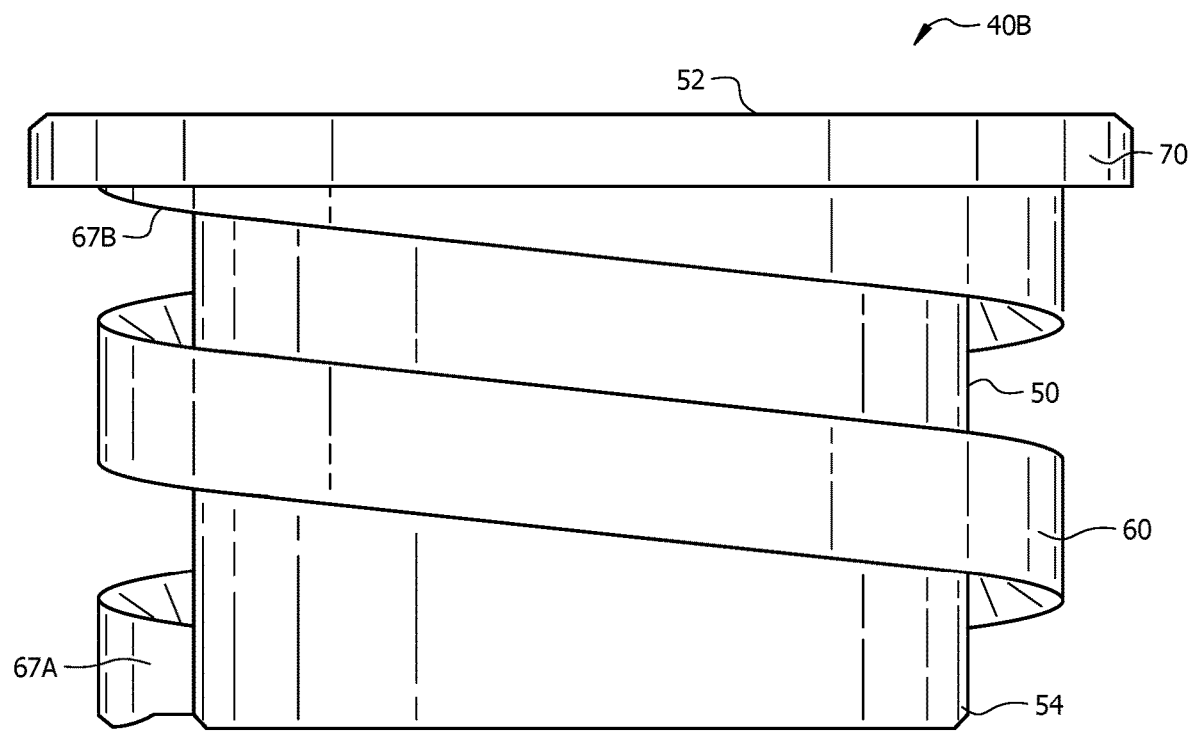
FIG. 1 illustrates an embodiment of a second interacting element including a body component and a thread component.

As illustrated in FIG. 1, certain embodiments of a first interacting element 40A may be in the form of a fastener element 70 and include a body component 50 and a thread component 60.

The body component 50 may include an end cap element 52 and a core body element 54. The core body element 54 may be configured as the foundation on which the thread component 60 is positioned or formed adjacent to the thread component 60.

Figure 5:
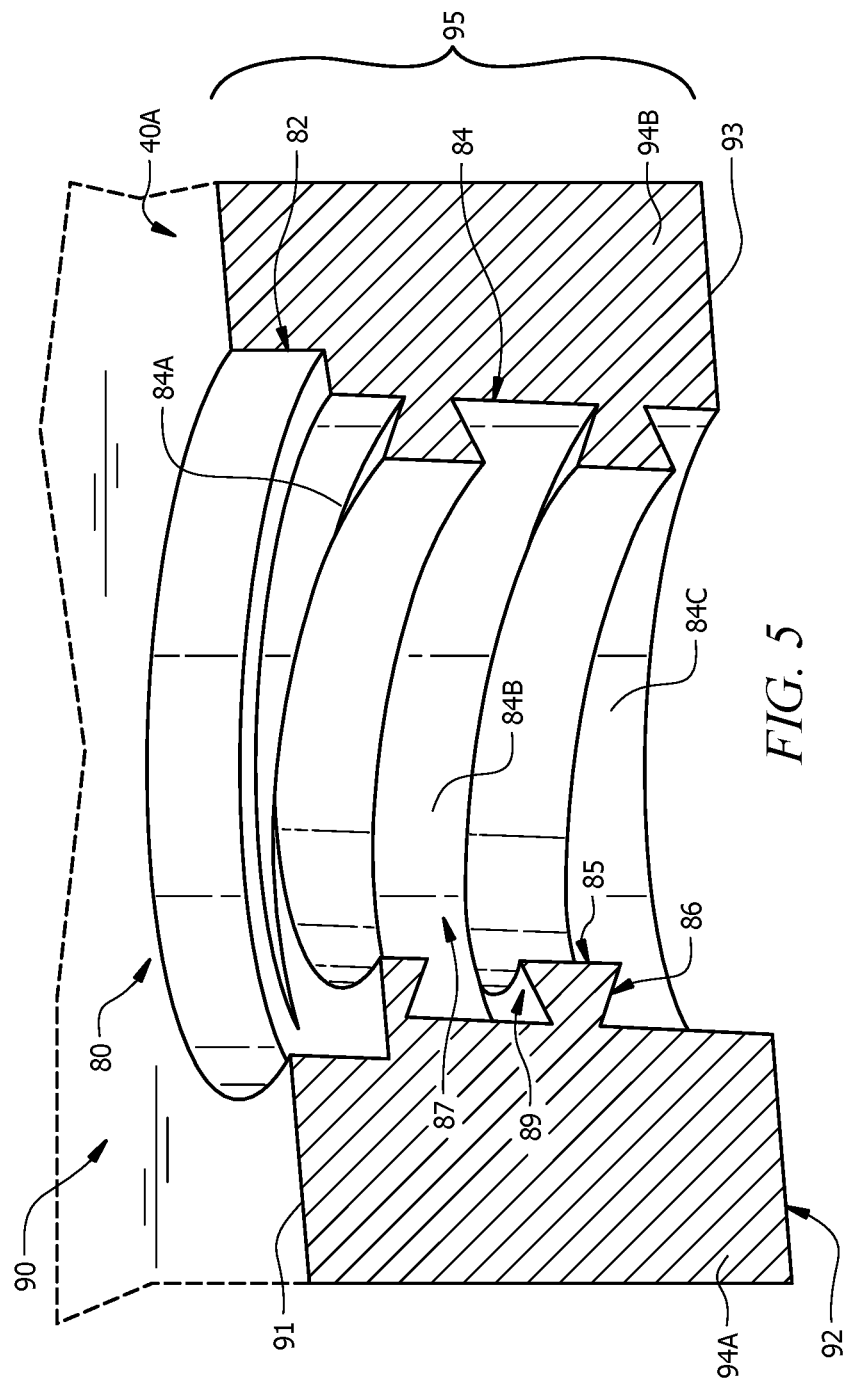
FIG. 5 illustrates an embodiment of a first interacting element, in the form of a plate.

The end cap element 52 may be configured to be relatively wider than the core body element 54 such that the end cap element 52 effectively forms the end of the thread component 60 and the first interacting element 40A cannot be rotated any further when the end cap element 52 meets with an end cap receiving element 82 in a second interacting element 40B (see e.g., FIG. 5). Other embodiments may include no end cap element or an end cap element that has the same or smaller cross-section diameter than the core body element 54. The thread component 60 may include a thread termination end 67A and a thread origination end 67B. The thread component 60 is positioned relative to the body component 50 such that upon rotating the first interacting element 40A, the thread component 50 is received by a thread receiving element 84 in the second interacting element 40B (see e.g., FIG. 5).

Figure 2:
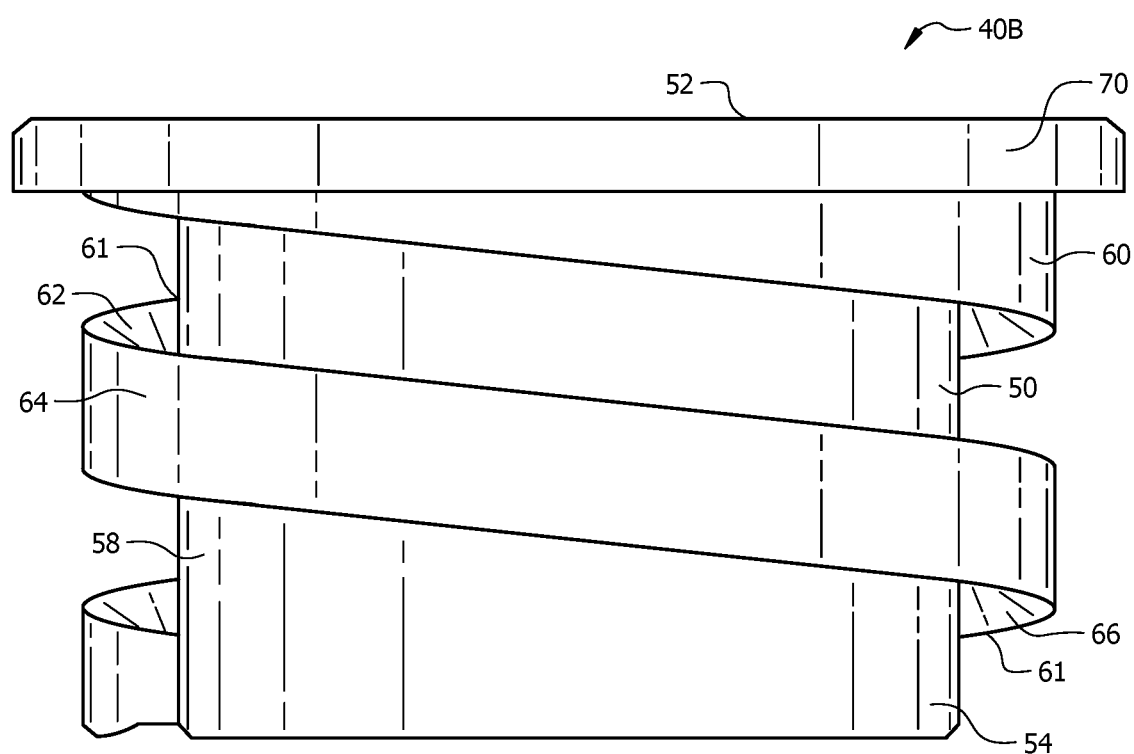
FIG. 2 illustrates additional features of a second interacting element including a body component and a thread component.

As illustrated in FIG. 2, the thread component 60 may include an outer thread surface 64 that may be generally parallel to the outer core body surface 58 of the core body element 54. In addition, the thread component 60 may include two or more side thread surfaces 61 configured to adjoin the outer thread surface 64 to the outer core body surface 58. The embodiment illustrated in FIG. 2 includes an upper thread surface 62 and a lower thread surface 66.

In certain embodiments, the entire first interacting element is a single unit formed by, for example, injection molding. In other embodiments, certain portions of the first interacting element are formed separately from the thread component and then the pieces are attached together.

Figure 3A:
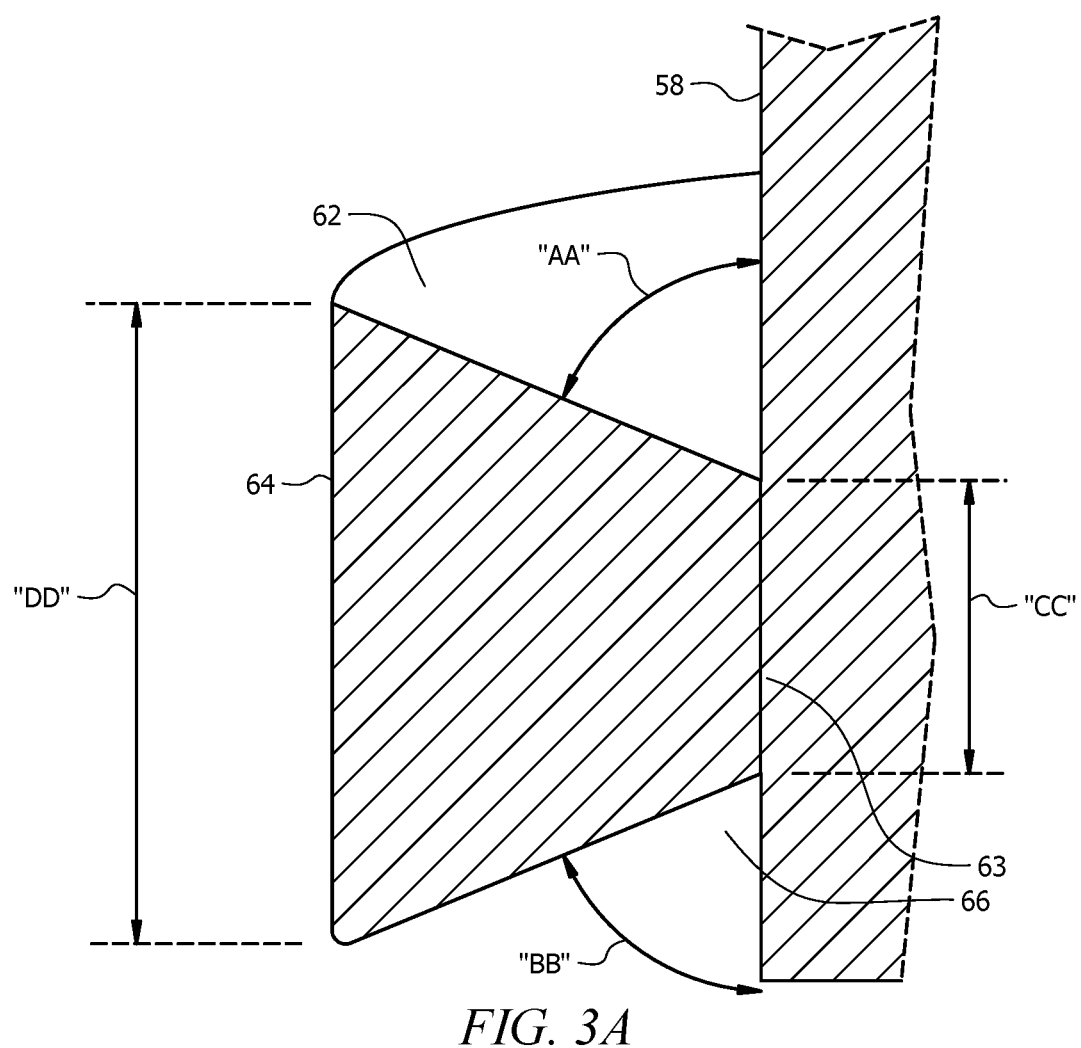
FIG. 3A illustrates a magnified view of a thread component.

As illustrated in FIG. 3A, a thread component 60 also may include a thread base surface 63. In certain embodiments, the thread base surface 63 is generally continuous with the outer core body surface 58. In other embodiments, the thread base surface 63 is a surface from the outer core body surface 58, but may be attached to the outer core body surface 58.

The angle between the upper thread surface 62 and the outer core body surface 58 is an upper thread angle "AA". The angle between the lower side thread surface 66 and the outer core body surface 58 is a lower thread angle "BB". In certain embodiments, the upper thread angle "AA" is between 45 and 90 degrees and the lower thread angle "BB" is between 45 and 90 degrees. In certain embodiments, the upper thread angle "AA" or the lower thread angle "BB" is 60 degrees.

As also illustrated in FIG. 3A, the length "CC" of the thread base surface 63 may be 0.102 millimeters (mm), 0.300 mm, or 0.700 mm. In certain embodiments, the length "DD" of the outer thread surface 64 is 0.318 mm, 0.875 mm, or 1.275 mm at its widest point. Of course, the length "DD" of the outer thread surface 64 may be shorter or longer, e.g., near the upper or lower sections of the core body element 54. As some examples, the ratio of the length "CC" of the thread base surface 63 to the length "DD" of the outer thread surface 64 may be 0.102 mm:0.318 mm, 0.300 mm:0.875 mm, or 0.700 mm:1275 mm.

In certain embodiments, the size of the thread component 60 is static throughout the entire thread component 60. In other embodiments, the thread base surface 63 (and possibly the outer thread surface 64) is smaller in length near the termination end 67A and larger in length near the origination end 67B (see FIG. 1). The length of each thread component surface may increase continuously (e.g. taper continuously) throughout the length of the thread component 60 or may increase more sharply only near the origination end 67B. Such embodiments are configured to permit locking the thread component 60 into a thread receiving element 84 (shown in FIG. 5) when the larger portion of the thread component meets with or is compressed into the thread receiving element 84.

Figure 3B:
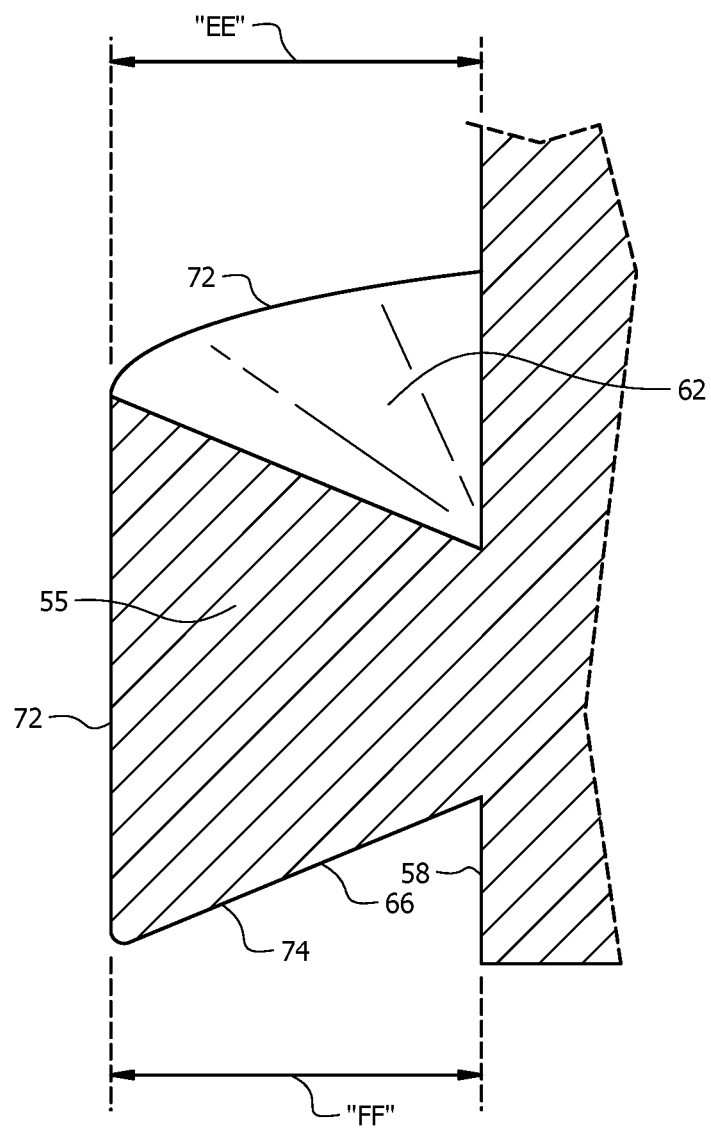
FIG. 3B also illustrates a magnified view of a thread component.

As illustrated in FIG. 3B, certain embodiments of the upper thread depth "EE" between the upper thread edge 72—that is, the edge at which the upper thread surface 62 meets the outer core body surface 58—may be 0.188 millimeters or 0.498 millimeters. Also, the lower thread depth "FF" between the lower thread edge 74—that is, the edge at which the lower side thread surface 66 meets the outer core body surface 58—may be 0.188 millimeters or 0.498 millimeters. The upper thread depth "EE" may be equal to, greater than, or less than the lower thread depth "FF".

The upper thread surface 62, lower thread surface 66, and outer thread surface 64 together form a thread profile 55 (from the side view). In certain embodiments, the thread profile 55 of the thread component 60 may be shaped in a dovetail shape. In certain embodiments of the present invention, any surface, including the upper thread surface 62, lower thread surface 66, outer thread surface 64, may be linear or curved.

Figure 4:
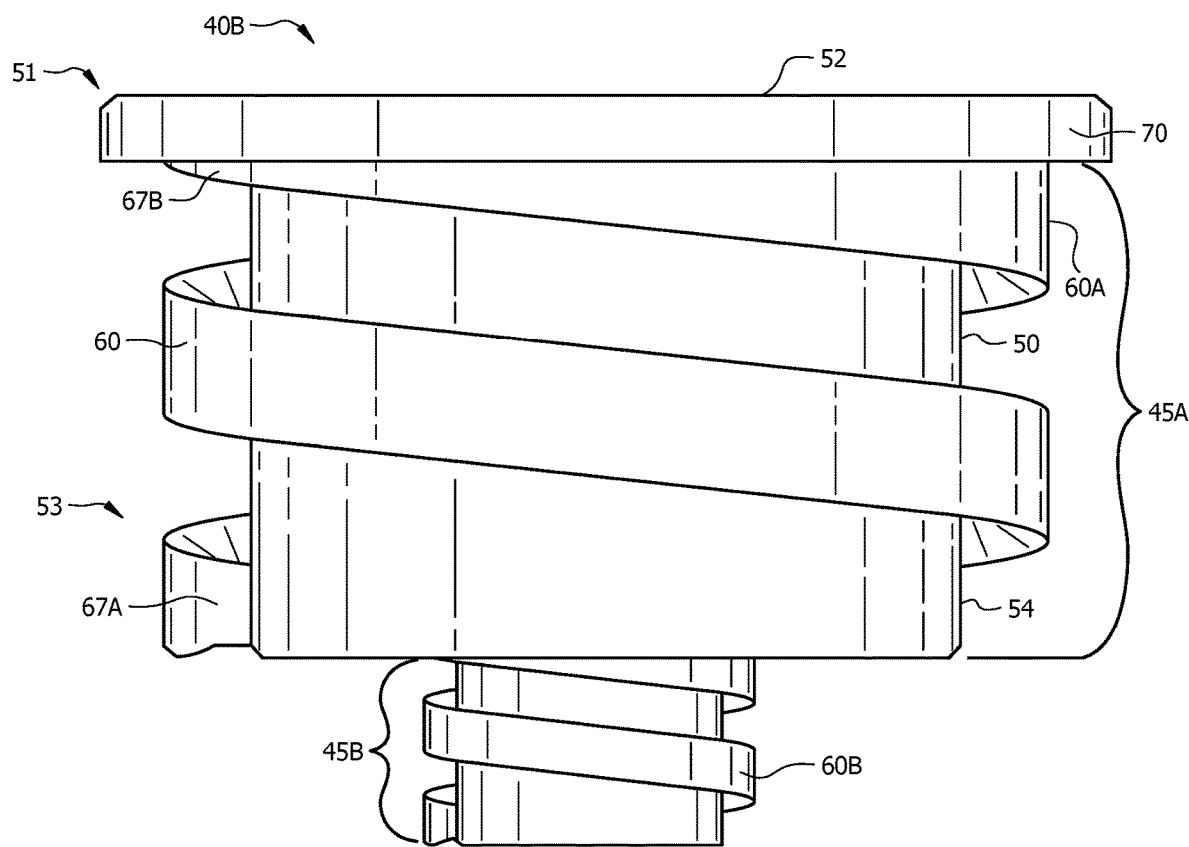
FIG. 4 illustrates an embodiment of a second interacting element having a first body component and a second body component.
Figure 8A:
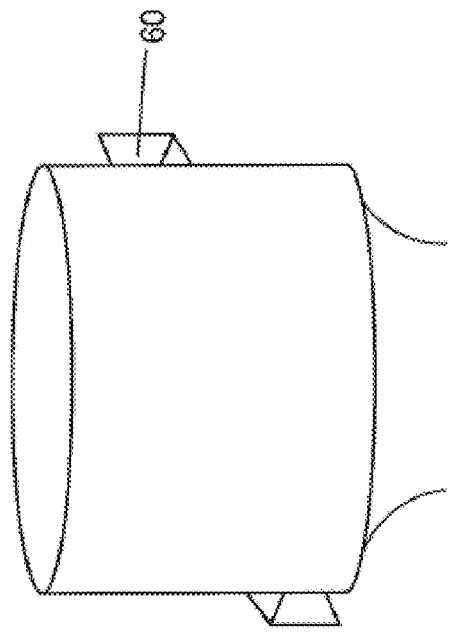
FIG. 8A illustrates an embodiment of a second interacting element having a first body component and a second body component, wherein the thread component on the first body component includes only a partial turn of a helix.
Figure 8B:
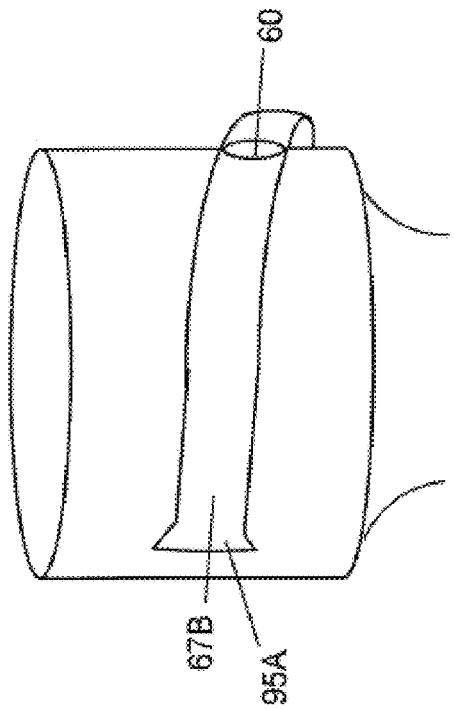
FIG. 8B illustrates an embodiment of a second interacting element having a first body component and a second body component, wherein the thread component on the first body component includes only a partial turn of a helix.
Figure 8C:
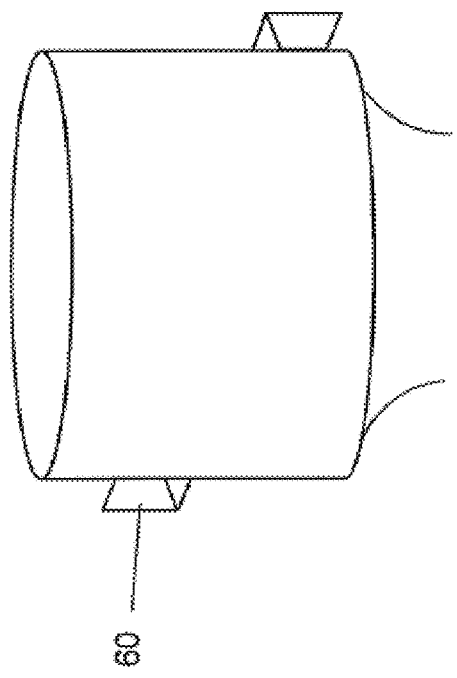
FIG. 8C illustrates an embodiment of a second interacting element having a first body component and a second body component, wherein the thread component on the first body component includes only a partial turn of a helix.

Certain embodiments of the present invention include two body components such as that shown in FIG. 4 (see also FIG. 8A, FIG. 8B). Turning to FIG. 4, a second body component 45B including a second thread component 60B configured to have a smaller cross-section diameter than the cross-section diameter of the first body component 45A including a first thread component 60A. Such embodiments may be configured such that the first body component 45A is configured to interact with a first thread receiving element such as a plate and the second body component 45B is configured to interact with a second thread receiving element such as a bone). For example, a plate 80 (see FIG. 14A) may be positioned relative to a bone to promote healing of the bone. The system of the present invention may be configured to stabilize the position of the plate relative to the bone. In such embodiments, the second thread component 60B of the second body component 45B may be any size or shape, including dovetail, rounded, v-shaped, pedicle, or other. In certain embodiments, the second thread component 60B has the same pitch as the pitch of the first thread component 60A of the first body component 45A. In other embodiments, the second thread component 60B has a greater pitch than the first thread component 60A such that the plate may be compressed against the bone as the core body component is interacting with the plate. An example of a pitch measurement of certain embodiments includes a 1.25 mm pitch on the second interacting element (or plate). Such a plate embodiment may have a peripheral surface length of 5 mm. The pitch of the thread component 60B on the second body component 45B may influence the pitch of the thread component 60A on the first body component 45A.

In certain embodiments, a first thread component 60A may be continuous with or connected to the second thread component 60B via a thread-thread connector (not shown). The thread-thread connector may have a tapered shape. In other embodiments, the two thread components 60A, 60B are completely integrated and have no connection. FIG. 5 illustrates a cross-section of an example of a second interacting element 40B in the form of a plate 80 such as that used for setting a bone. The plate 80 may include an end cap receiving element 82 and a thread receiving element 84. The end cap receiving element 82 may be generally complementary to the size and shape of the end cap element 52. The thread receiving element 84 may be generally complementary to the size and shape of the thread component 60.

Each thread receiving element 84 may include an outer receiving surface 85, upper receiving surface 86, inner receiving surface 87, and lower receiving surface 89. In certain embodiments of the present invention, any surface, including the outer receiving surface 85, upper receiving surface 86, inner receiving surface 87, and lower receiving surface 89 may be linear or curved.

Figure 7:
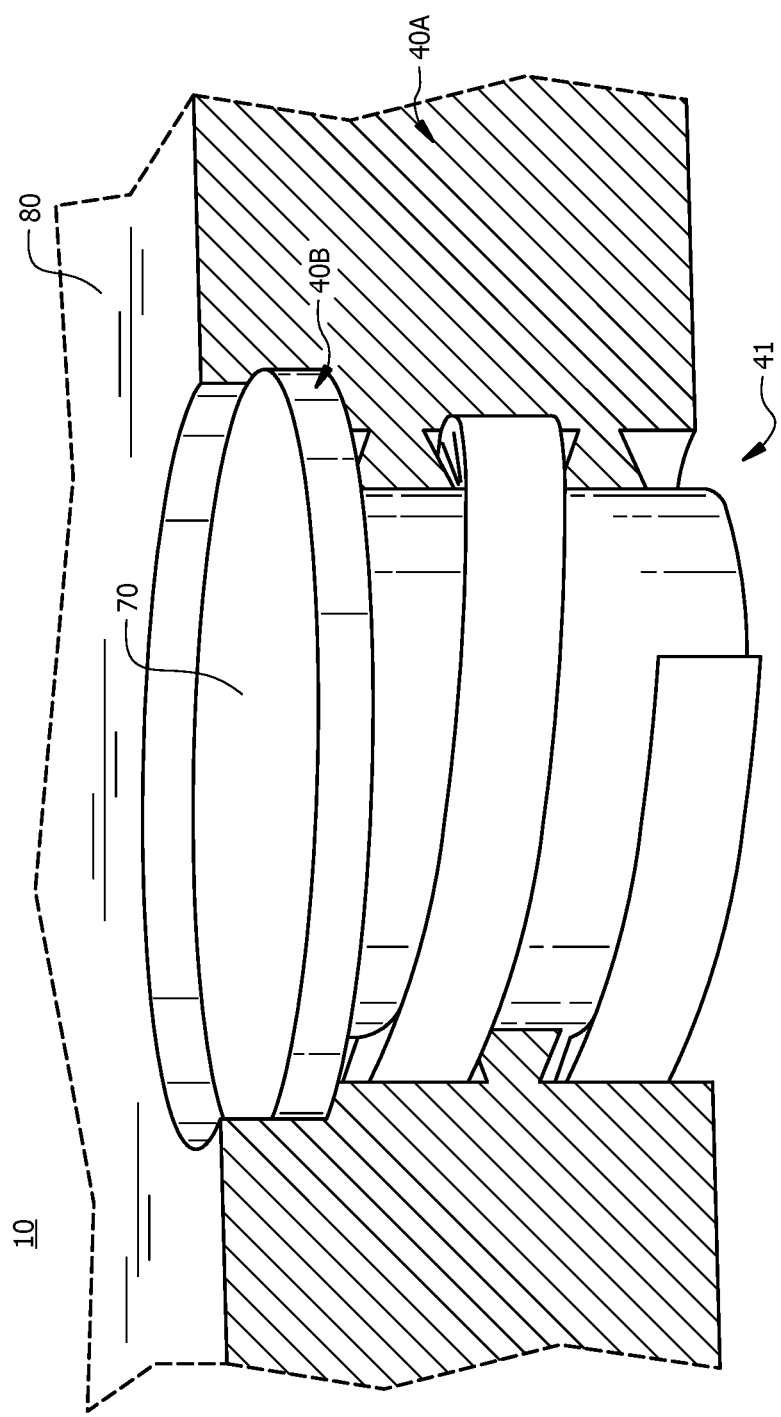
FIG. 7 illustrates a second interacting element positioned relative to a first thread receiving element of a first interacting element.

When the thread component 60 is received within the thread receiving element 84 (as illustrated in FIG. 7), the outer receiving surface 85 is generally adjacent to or flush with the outer core body surface 58 of the core body element 54, the upper receiving surface 86 is generally adjacent to or flush with the lower thread surface 66, the inner receiving surface 87 is generally adjacent to or flush with the outer thread surface 64, and the lower receiving surface 89 is generally adjacent to or flush with the upper thread surface 62.

In embodiments in which the thread component 60 includes multiple helical turns, the thread receiving element 84 may include more than one thread receiving element 84, such as a first thread receiving element 84A, a second thread receiving element 84B, and a third thread receiving element 84C. Any number of thread receiving elements 84 is contemplated. In the embodiment illustrated in FIG. 5, the first thread receiving element 84A is positioned closest to the upper surface 90 of the plate 80. The third thread receiving element 84C is positioned closest to the lower surface 92 of the plate 80. A second thread receiving element 84B is positioned between the first thread receiving element 84A and the third thread receiving element 84C. The third thread receiving element 84C may be tapered in size such that the respective portion of the thread component 60 may be stabilized in position. In certain embodiments, the one or more thread receiving elements 84 are positioned along the periphery of plate 80 such that only certain portions of the thread component 60 are enclosed within a thread receiving element 84. One or more thread receiving elements 84 may be flanked by a first peripheral surface 94A and a second peripheral surface 94B of the plate 80.

Figure 6C:
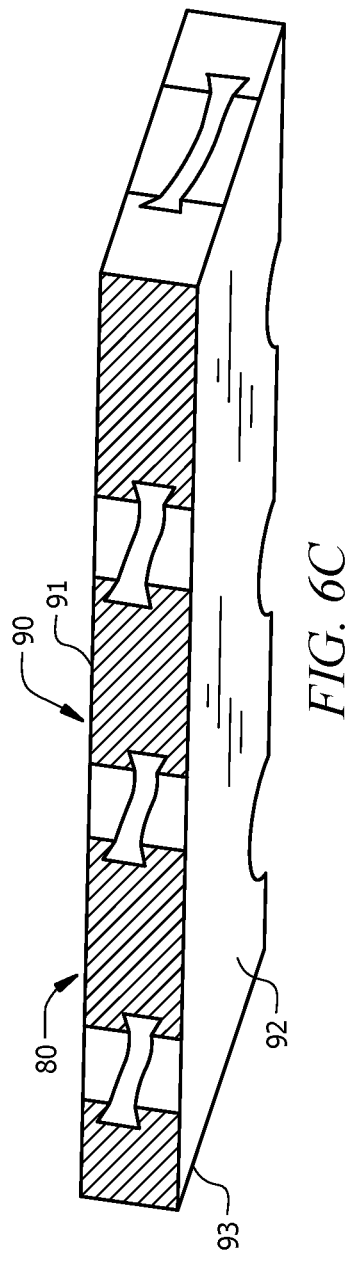
FIG. 6C illustrates a perspective view of an embodiment of a first interacting element in the form of a plate, including a plurality of thread receiving elements.
Figure 6D:
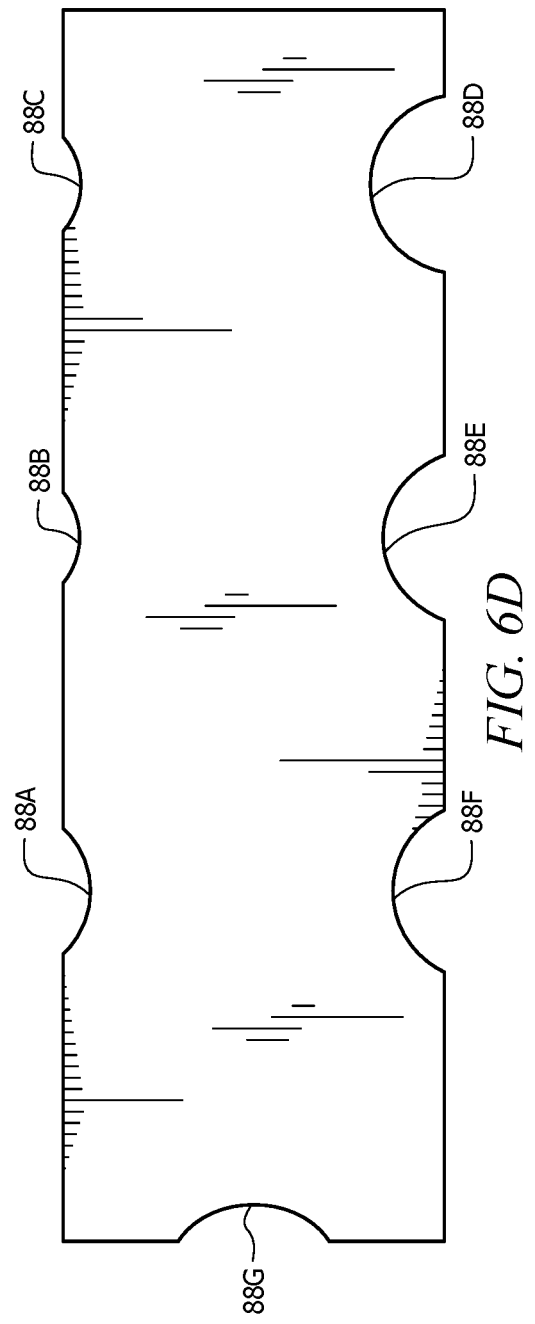
FIG. 6D illustrates a top view of an embodiment of a first interacting element in the form of a plate, including a plurality of thread receiving elements.

The peripheral surfaces 94A, 94B meet with the upper surface 90 at an upper edge 91 and a lower surface 92 at a lower edge 93. Additional embodiments may be configured to include only one thread receiving element 84 such as that illustrated in FIG. 6A. Certain other embodiments of a bone-setting plate 80 according to the invention include more than one thread receiving element 84 as illustrated in FIG. 6B-FIG. 6D. The thread receiving element 84 embodiments shown in FIG. 6A-FIG. 6D may receive a thread component 60 shaped in multiple helical turns, for example, turns that start at or near the bottom side of the first body component and end at or near the top side of the first body component.

Alternatively, the thread receiving element 84 embodiments shown in FIG. 6A-FIG. 6D may receive a thread component 60 shaped in a single helical turn or less than a full helical turn. For purposes of this application, a "full helical turn" is a complete 180 degree rotation in around a cylindrical axis. (Obviously, if the rotation was in a flat plane instead of a cylindrical axis, the shape would be a circle, not a helix.)

FIG. 6D shows a few examples of shape configurations of a thread receiving element 84 or, more specifically, the top profile shown by 88 of a thread receiving element 84. Clearly, the top profile 88 may form a general arc-shape configuration. In certain embodiments, the arc-shape configuration may be any portion of a circle from 360 degrees to 90 degrees, including, for example, a three-quarters-circle shape (270 degrees), half-circle-shape (180 degrees), third-circle shape (120 degrees), or fourth-circle shape (90 degrees). While the embodiment in FIG. 60 illustrates multiple thread receiving elements 84, each having a different arc-shape configuration 88A-88G, it is contemplated that plate 80 may include a plurality of thread receiving elements 84 each having the same arc-shape configuration 88. FIG. 7 illustrates a system 10 including a first interacting element 40A configured as a fastener element 70 positioned within the second interacting element 40B configured as a plate 80 for setting bones. Certain embodiments include a third interacting element 40C, which may be a bone. For example, the fastener element 70 may be configured to interact with both a plate 80 and a bone—shown as third interacting element 40C. In certain embodiments, the fastener element 70 may be configured to interact with only the plate 80. In certain other embodiments the fastener element 70 may be configured to only interact with bone (i.e., without the use of plate 80).

Figure 8D:
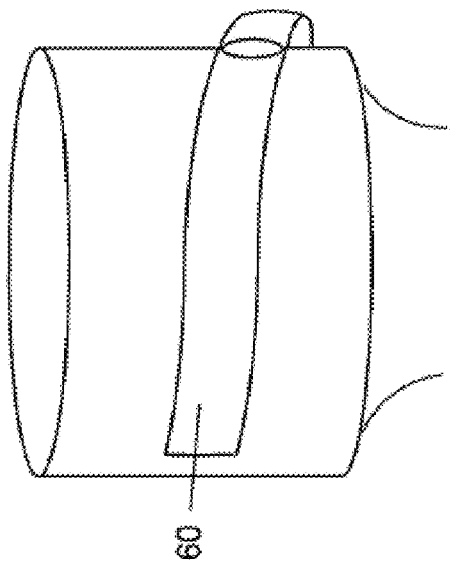
FIG. 8D illustrates an embodiment of a second interacting element having a first body component and a second body component, wherein the thread component on the first body component includes only a partial turn of a helix and the thread component includes a stop element.

As illustrated in FIG. 8A and FIG. 8B, the helical shape of the thread component 60 may be left-handed or right-handed. Also illustrated in FIG. 8A, FIG. 8B, FIG. 8C and FIG. 8D, the thread component 60 may be sized to include only a partial turn of a helix shape. As also illustrated in FIG. 8D, the thread origination end 67B may include an enlarged portion to form a stop element 95A such that the thread component 60 cannot move further into the thread receiving component 84.

Figure 9A:
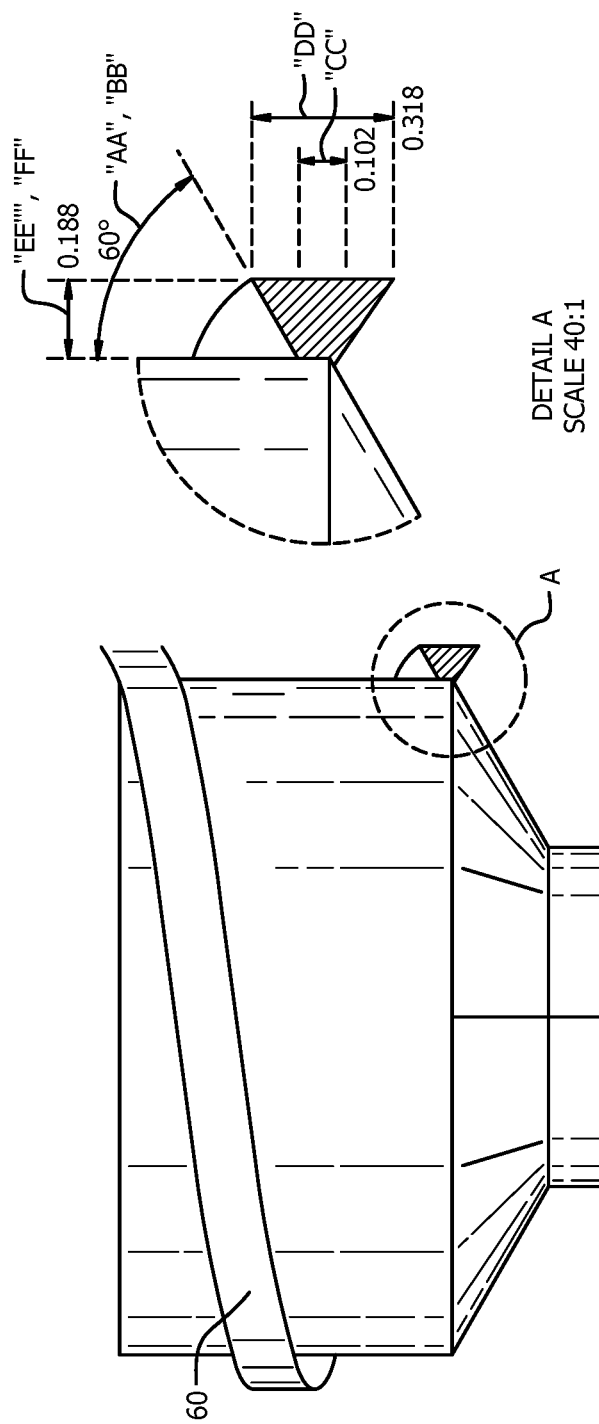
FIG. 9A illustrates an embodiment of a second interacting element having a first body component and a second body component.
Figure 9B:
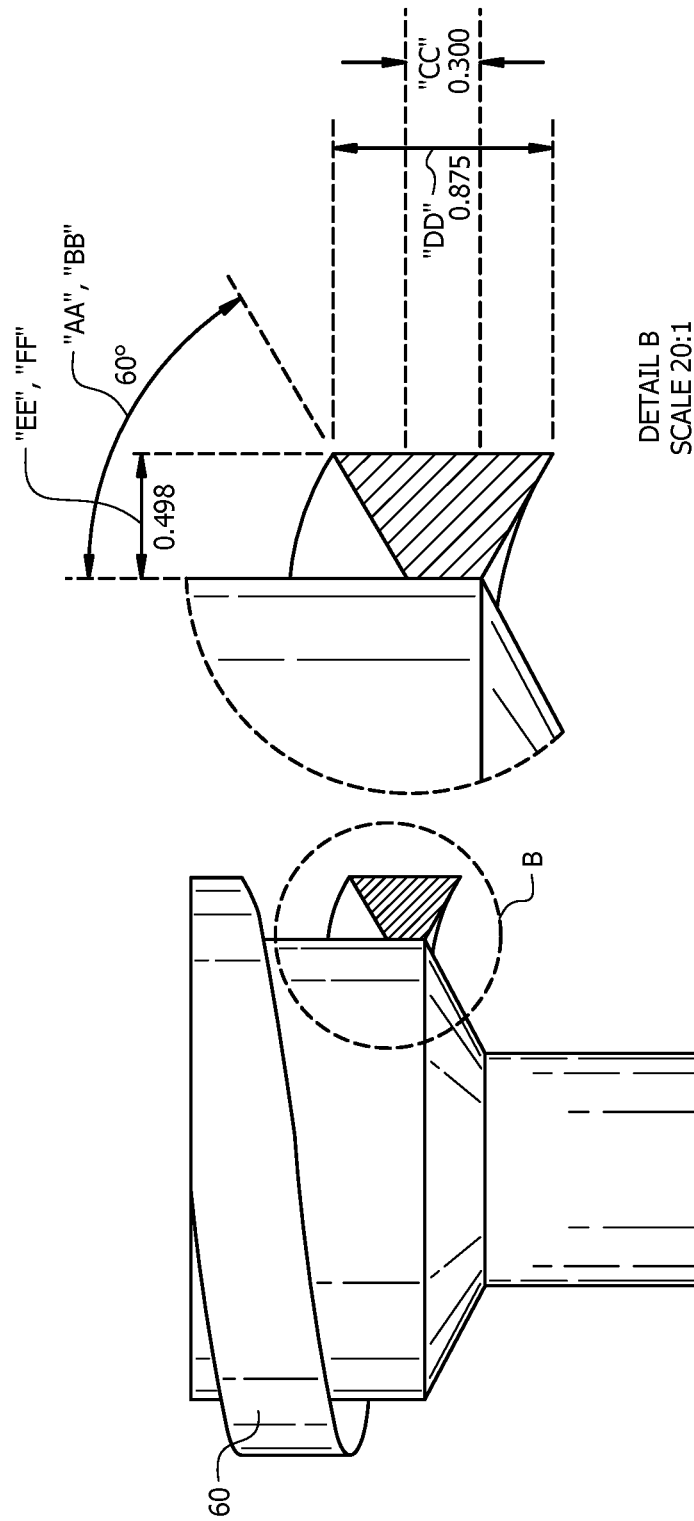
FIG. 9B illustrates an embodiment of a second interacting element having a first body component and a second body component.
Figure 9C:
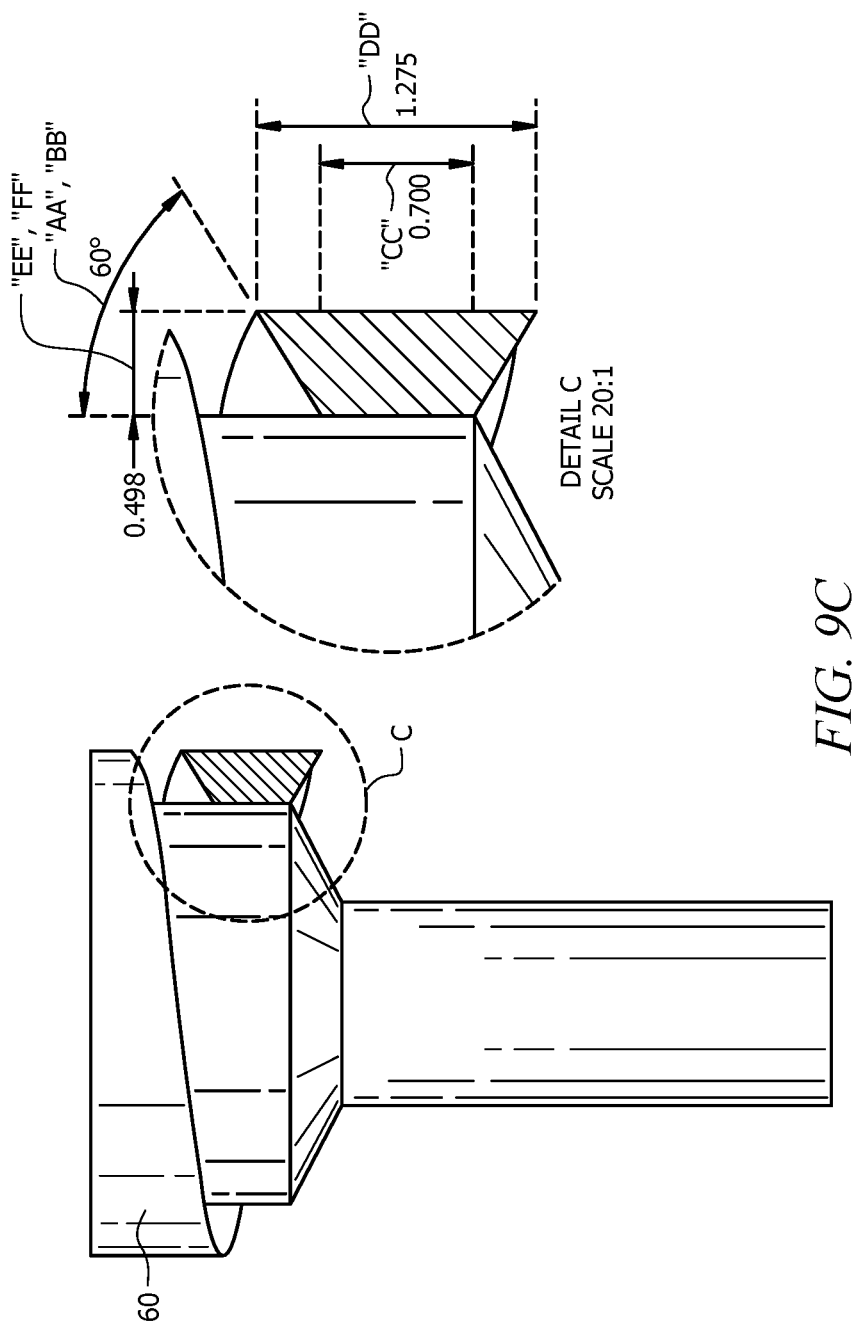
FIG. 9C illustrates an embodiment of a second interacting element having a first body component and a second body component.

FIG. 9A, FIG. 9B, and FIG. 9C illustrate additional embodiments of the present invention. While certain embodiments are identified as having specific measurements in millimeters (mm), each part of the invention may be sized and shaped for any particular purpose. Specifically, in certain embodiments, the measurements are scaled up or scaled down based on the ratios illustrated in FIGS. 9A-9C, sometimes for a particular purpose (e.g., stronger connection or more flexibility). In addition, the ratios between components may be altered to achieve a particular purpose (e.g., stronger connection or more flexibility) as well. For example, turning to FIG. 9A, the upper thread angle ("AA") and/or lower thread angle ("BB") may be about 60 degrees. The length of the thread base surface ("CC") may be about 0.102 mm and the length of the outer thread surface ("DD") about 0.318 mm. The upper thread depth ("EE") and/or lower thread depth ("FF") may be about 0.188 mm. Turning to FIG. 9B, the upper thread angle ("AA") and/or lower thread angle ("BB") may be about 60 degrees. The length of the thread base surface ("CC") may be about 0.300 mm and the length of the outer thread surface ("DD") about 0.875 mm. The upper thread depth ("EE") and/or lower thread depth ("FF") may be about 0.498 mm.

In another example shown in FIG. 9C, the upper thread angle ("AA") and/or lower thread angle ("BB") may be about 60 degrees. The length of the thread base surface ("CC") may be about 0.700 mm and the length of the outer thread surface ("DD") about 1.275 mm. The upper thread depth ("EE") and/or lower thread depth ("FF") may be about 0.498 mm.

Figure 10A:
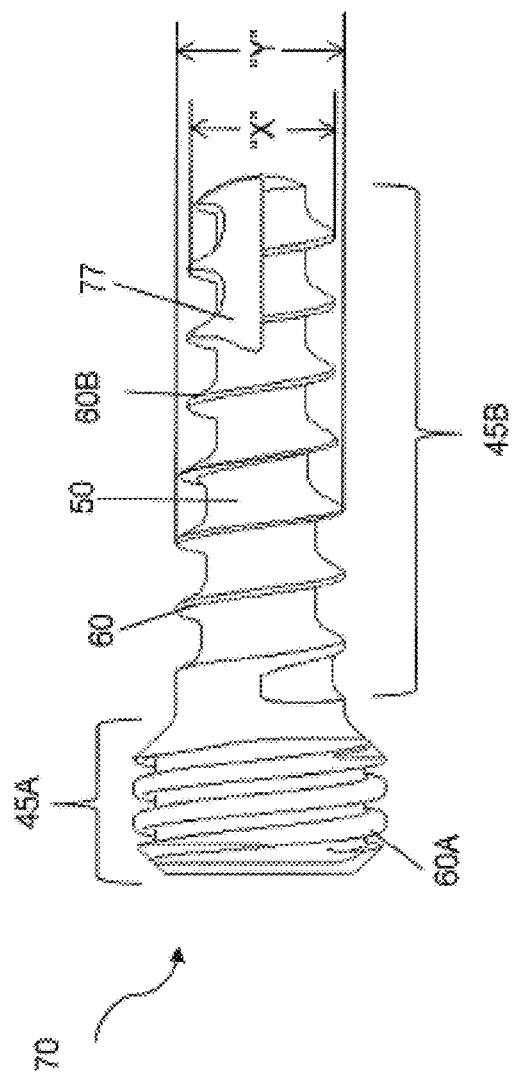
FIG. 10A illustrates an embodiment of a second interacting element having a first body component and a second body component.
Figure 10B:
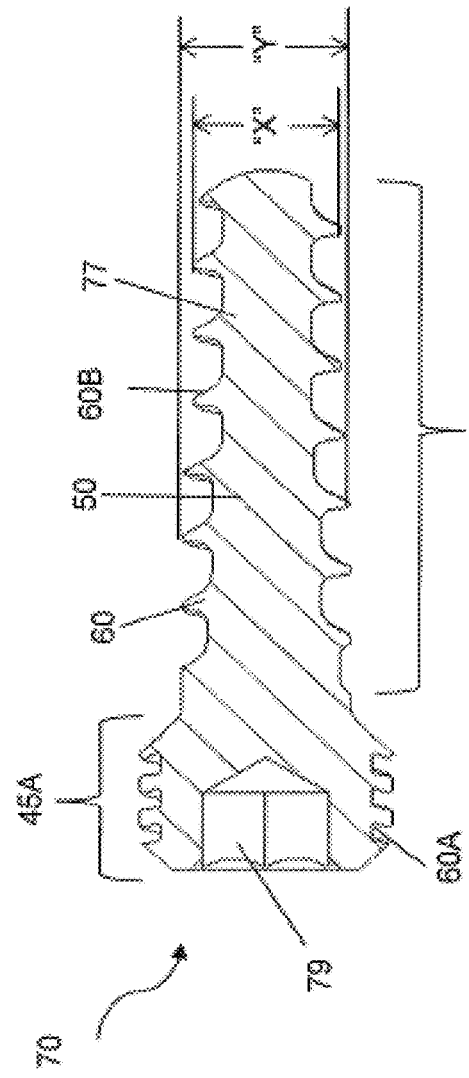
FIG. 10B illustrates a cross-sectional view of an embodiment of a second interacting element having a first body component and a second body.

FIG. 10A and FIG. 10B illustrates an embodiment of fastener element 70 including a body component 50 and a thread component 60. In particular, the fastener element 70 includes a first body component 45A and a second body component 45B. The first body component 45A includes a first thread component 60A configured to interface with a plate 80 (not shown). The second body component 45B includes a second thread component 60B configured to interface with bone (not shown). As shown in this embodiment, the body component 50 includes different cross-section diameters as shown by "X" and Y. Although two cross-section diameters are shown, any number of different cross-section diameters of the body component is contemplated. A body component 50 with varying cross-section diameter provides for optimum anchoring of the assembly to the bone. Also shown in this embodiment is a cutting flute element 77 to facilitate a self-tapping capability. As shown within the first body component 45A, a hex component 79 allows for manipulation and placement of the fastener element such as by using a hex socket. As shown more particularly in FIG. 10B, the thread component 60A includes a one-sided dovetail thread arrangement with variable pitch.

Figure 11A:
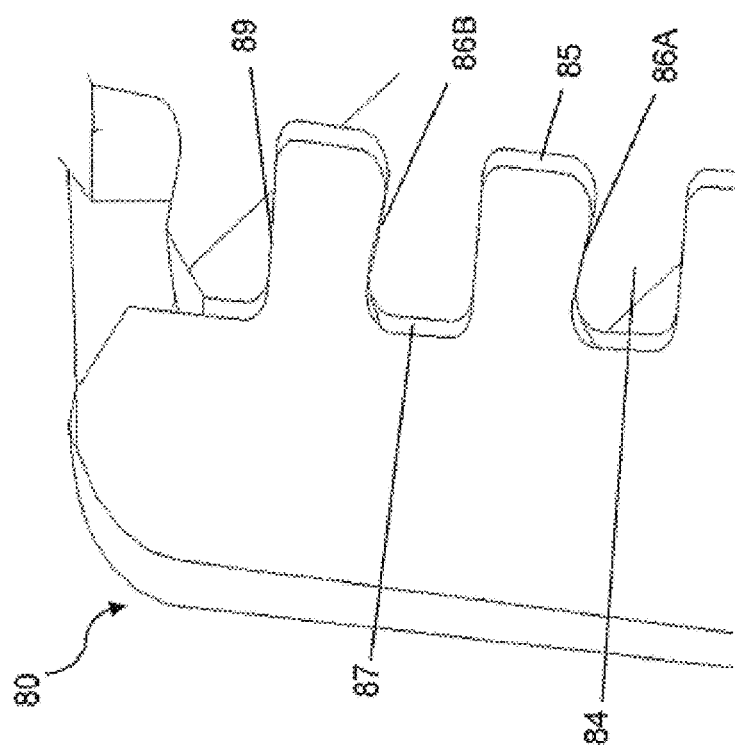
FIG. 11A illustrates an exploded view of a plate including a thread receiving element.
Figure 11B:
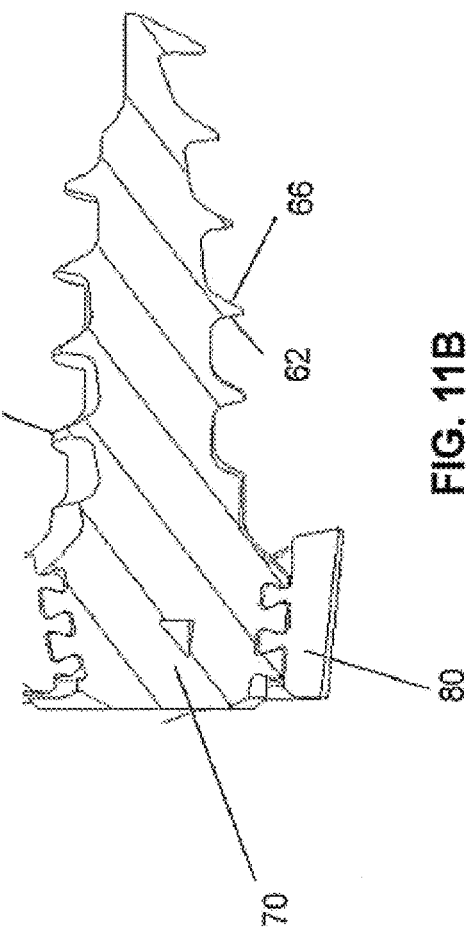
FIG. 11B illustrates an embodiment of the second interacting element, in the form of a fastener, engaged with the thread receiving element of the first interacting element.

FIG. 11A illustrates an exploded view of a plate 80 including a thread receiving element 84. Each thread receiving element 84 includes an outer receiving surface 85, upper receiving surface 86, inner receiving surface 87, and lower receiving surface 89. In this particular embodiment, the upper receiving surface 86A is of a different pitch than upper receiving surface 86B to accommodate the varying pitch of the fastener element 70. Thus, the first threads of the fastener element 70 to engage the upper receiving surface 86A of receiving element 84 of the plate 80 have a sliding fit. In contrast, the last threads of the fastener element 70 to engage the upper receiving surface 86B of receiving element 84 of the plate 80 have an interference fit to lock the plate 80 and fastener element 70 together as shown more specifically in FIG. 11B. FIG. 11B illustrates a cross-section view of an embodiment of a fastener element 70 engaged with the thread receiving element 84 of a plate. The fastener element 70 shown in FIG. 11B has two-sided dovetail threads 60, i.e., the upper thread surface 62 and a lower thread surface 66 are each of a dovetail shape.

FIG. 12A, FIG. 12B, FIG. 12C illustrate a plate element 80 according to one embodiment of the invention. As shown, plate 80 including one or more aperture elements 71 through which fastener elements 70 engage. A window element 73 provides for intra-operative as well as post-operative visualization. Intra-operative visualization may include, for example, visualization of a bone graft, surgical tools, or other surgical implements during the surgical procedure such as an endplate attached to the plate 80 via fastener elements. Post-operative visualization may include, for example, visualization on x-rays subsequent to the surgical procedure.

FIG. 12B illustrates a lordotic curve 75 and FIG. 12C illustrates an endplate curve 76, both of which coincide or match the curvature of certain features such as an endplate or spine.

Figure 13:
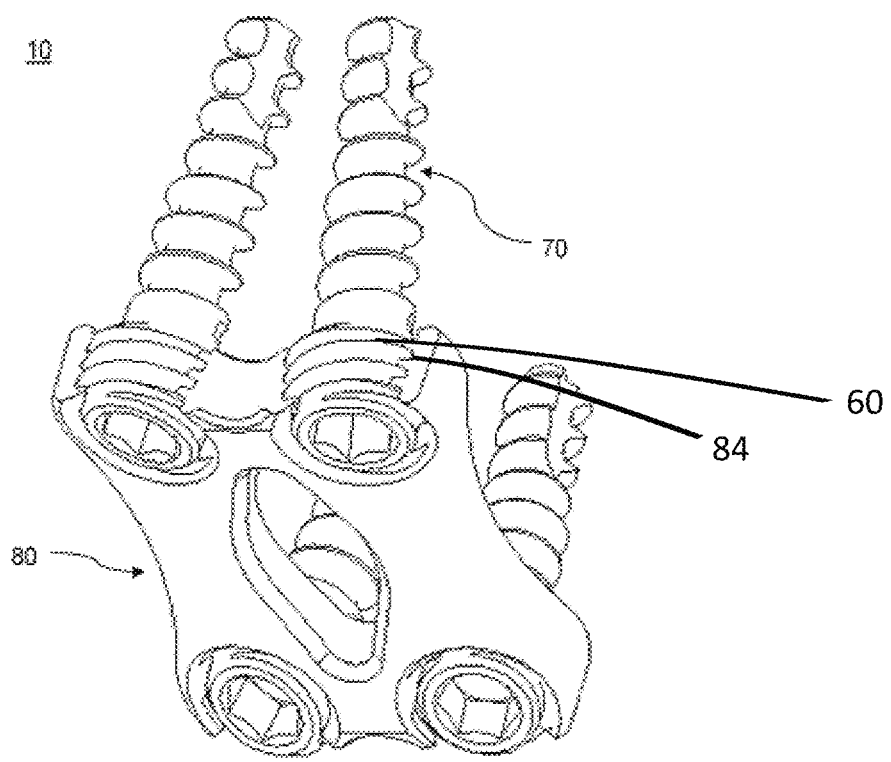
FIG. 13 illustrates an assembly view of a first interacting element in the form of a plate and having a plurality of second interacting elements in the form of fasteners disposed within apertures of the first interacting element.
Figure 14B:
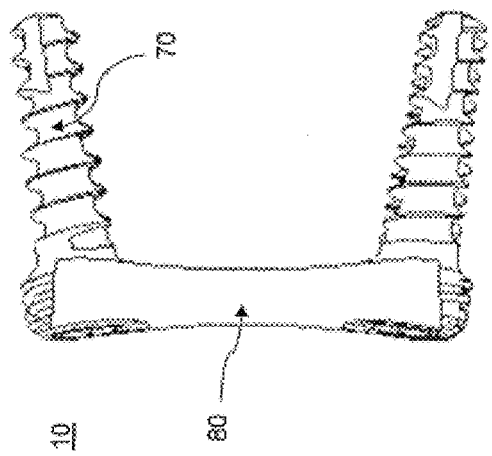
FIG. 14B illustrates a horizontal side view of the assembly shown in FIG. 13.
Figure 14C:
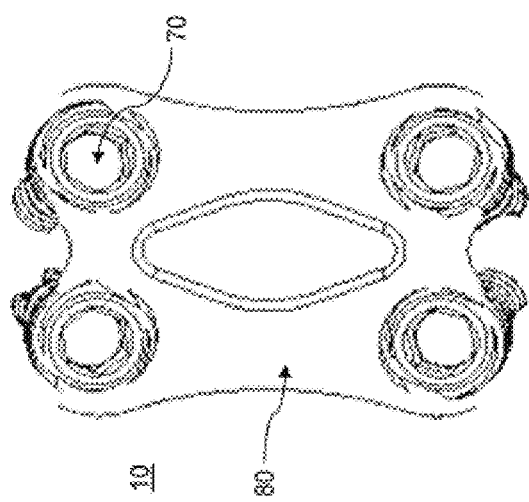
FIG. 14C illustrates a top view of the assembly shown in FIG. 13.
Figure 14A:
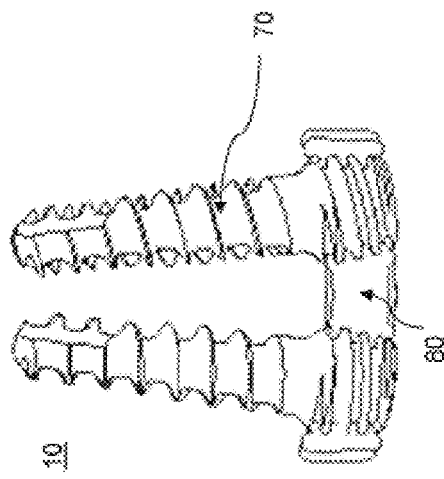
FIG. 14A illustrates a longitudinal side view of the assembly shown in FIG. 13.

FIG. 13 illustrates an assembled system 10 including plate element 80 and a plurality of fastener elements 70. FIG. 14A illustrates a cross-section side view of the assembly 10, FIG. 14B illustrates a side view of the assembly 10, and FIG. 14C illustrates a top view of the assembly 10. The trajectories of the fastener elements 70 can be seen in FIG. 13, FIG. 14A, FIG. 14B. The fastener elements 70 are driven with a hex socket until they are flush with the plate 80. In particular, this embodiment of the invention illustrates the aperture elements 71 surround approximately 70% of the end cap element 52 of the fastener element 70 leaving the superior-most and inferior-most parts of the fastener elements 70 exposed. This low profile embodiment allows for secure engagement between the fastener elements 70 and plate 80, which may reduce the risk of pain and discomfort.

While the disclosure is susceptible to various modifications and alternative forms, specific exemplary embodiments of the present invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A system for securing two interacting elements to each other, comprising:
    a first interacting element including a body component and a thread component, wherein the thread component has an upper thread surface, a lower thread surface, an outer thread surface, and the thread component is positioned at least partially around a core body element;
    a second interacting element including a thread receiving element configured to receive the thread component, wherein the thread receiving element is positioned in an outer peripheral surface of the second interacting element and includes a circumferential extent that is greater than 180 degrees and less than 360 degrees;
    wherein the upper thread surface, lower thread surface, and outer thread surface form a profile of the thread component; and
    wherein the profile of the thread component is larger near a termination end relative to the thread profile of the thread component near the origination end to act as a rotational stop to stop insertion of the first interacting element.

2. The system of claim 1, wherein the thread receiving element is configured to receive a portion of the thread component that forms less than a full turn.

3. The system of claim 1, wherein the thread receiving element is configured to receive only half of a turn of the thread component.

4. The system of claim 1, wherein the thread receiving element is configured to receive a portion of the thread component that forms only a third of a turn.

5. The system of claim 1, wherein the thread receiving element is configured to receive a portion of the thread component that forms only a fourth of a turn.

6. The system of claim 1, wherein the thread receiving element includes an upper receiving surface, an inner receiving surface, and a lower receiving surface, which together form a thread receiving profile, and the thread receiving profile is smaller near a receiving termination end relative to a receiving origination end of the thread receiving element to act as a rotational stop.

7. A system for maximizing connection strength between two interacting elements, comprising:
    a first interacting element including a body component and a thread component, wherein the thread component at least partially encircles the body component, the thread component having a thread origination end and a thread termination end;
    a second interacting element including a thread receiving element configured to receive the thread component, the thread receiving element having i semicircular shape that is greater than 180 degrees but less than 360 degrees;
    wherein the thread component includes an upper thread surface, an inner thread surface, and a lower thread receiving surface, which together form a thread profile; and
    wherein the thread profile of the thread component is larger near a termination end relative to the thread profile of the thread component near an origination end to act as a rotational stop to stop insertion of the first interacting element.

8. The system of claim 7, wherein the thread receiving element is positioned in an outer peripheral surface of the second interacting element.

9. The system of claim 8, wherein the thread receiving element is configured to receive a portion of the thread component that forms less than a full turn.

10. The system of claim 8, wherein the thread receiving element is configured to receive a portion of the thread component that forms only half of a turn.

11. A system for maximizing connection strength between two interacting elements, comprising:
- a first interacting element, the first interacting element including a core body element and a thread component at least partially positioned around the core body element;
- the thread component having a cross-sectional thread profile comprised of an upper thread surface, a lower thread surface, an outer thread surface;
- a second interacting element, the second interacting element having a main body defined by an upper surface, a lower surface, and an outer peripheral surface that adjoins the upper and lower surfaces and establishes an outer lateral boundary of the second interacting element;
- an aperture disposed through the upper and lower surfaces of the main body, the aperture also passing through the outer peripheral surface of the main body resulting in the aperture having a semicircular shape; and
- a thread receiving element disposed within the aperture, wherein the thread receiving element includes a semicircular shape that is greater than 180 degrees but less than 360 degrees in circumference and is configured to receive the thread component, such that a region of the first interacting element, that is diametrically opposed from a region of the thread component received within the thread receiving element when the first interacting element engages the second interacting element, remains exposed to an ambient environment;
- wherein the thread receiving element includes an upper receiving surface, an inner receiving surface, and a lower receiving surface, which together form a thread receiving profile; and
- wherein the thread receiving profile is smaller near a receiving termination end relative to a receiving origination end of the thread receiving element to act as a rotational stop to stop insertion of the first interacting element.

* * * * *